(12) United States Patent
Bonne et al.

(10) Patent No.: US 6,178,811 B1
(45) Date of Patent: Jan. 30, 2001

(54) QUASI-STATIC VISCOMETER

(75) Inventors: Ulrich Bonne, Hopkins; Tom M. Rezachek, Cottage Grove; David Kubisiak, Chanhassen, all of MN (US)

(73) Assignee: Honeywell International Inc., Morristown, NJ (US)

(*) Notice: Under 35 U.S.C. 154(b), the term of this patent shall be extended for 0 days.

(21) Appl. No.: 09/266,681

(22) Filed: Mar. 11, 1999

(51) Int. Cl.[7] ................................................ G01N 11/08
(52) U.S. Cl. .............................. 73/54.04; 73/54.01
(58) Field of Search ........................... 73/54.01, 54.04, 73/54.05, 54.06, 54.09, 861.18, 861.19

(56) References Cited

U.S. PATENT DOCUMENTS

| | | | | |
|---|---|---|---|---|
| 4,384,792 | * | 5/1983 | Sommers et al. ...................... | 374/36 |
| 4,441,358 | * | 4/1984 | Osborne .................................. | 73/55 |
| 4,627,271 | * | 12/1986 | Abbott et al. ......................... | 73/55 |
| 4,750,351 | * | 6/1988 | Ball ........................................ | 73/55 |
| 4,922,542 | * | 5/1990 | Sapiejewski ........................ | 381/187 |
| 5,323,638 | * | 6/1994 | Langdon ................................ | 73/32 |
| 5,486,107 | | 1/1996 | Bonne .................................. | 431/121 |
| 5,847,268 | * | 12/1998 | Ball ..................................... | 73/54.09 |

OTHER PUBLICATIONS

W.A. Wakeham, A. Nagashima, J.V. Sengers. *Measurement of the Transport Properties of Fluids*. Published by Blackwell Scientific in Oxford, London. (1991) pp. 1–109.
U. Bonne, D. Kubisak. Microsensors for Fluid Properties. *Scientific Honeyweller:* Sensors Issue (1996), p. 21.

* cited by examiner

*Primary Examiner*—Hezron Williams
*Assistant Examiner*—C D Garber
(74) *Attorney, Agent, or Firm*—John G. Shudy, Jr.

(57) ABSTRACT

A viscometer having a fluid volume-displacer or driver, such as a speaker membrane, and a pressure sensor or detector, such as a microphone membrane, forming the inside surfaces of a cavity that is sealed from the ambient environment of the viscometer except for a controlled leak such as a capillary tube. An electrical signal from the sensor or detector is processed to indicate viscosity of the fluid in the cavity. Additionally determined from the viscosity are heating value, oxygen demand and other thermophysical properties of the fluid. Also, absolute pressure is derived after viscosity is determined.

23 Claims, 9 Drawing Sheets

QUASI-STATIC VISCOMETER

BACKGROUND

The present invention pertains to viscosity detectors and particularly to delta-pressure-based sensors. More particularly, the invention pertains to viscosity sensors for determining the oxygen demand (for complete combustion) of a gaseous or liquid fuel for combustion purposes.

Existing and recently proposed quasi-static viscometers are either fluid (i.e., gas or liquid) density and pressure-dependent and costly (such as vibrating wire or quartz crystal-based viscometers). Other viscometers suffer from additional fluid property dependencies (e.g., those involving thermally-driven capillary flow), are prone to drift due to deteriorating and leaky valves (as in viscometers dependent on capillary flow driven by periodic refill from a source of pressurized gas, valve closure and decay observation), or depend on their orientation (as with the falling ball viscometer).

The proposed sensor measures a known property of fluids, viscosity. When applied to a combustion control system, it enables feed-forward operation and sensing in the mild pre-combustion environment; it is low-cost because the property can be simply proportional to the measured signal (in one preferred measurement approach) and it relates also simply to Wobbe number, oxygen demand or heating value of the fuel, so that the sensing error makes a relatively small contribution to the total combustion control error.

This invention involves the use or application of a known property, viscosity, to combustion control. It is also about using a preferred approach to viscosity measurement to that application.

Viscosity, $\eta$, may be known best for its linear relation to laminar volumetric flow (dV/dt) and pressure drop, $\Delta p$, in a capillary (of radius, $r_c$, and length, $L_c$), as shown in equation (1).

$$dV/dt = \pi \Delta p r_c^4 / (8 L_c \eta) \quad (1)$$

One first notes the potential of viscosity as an individual property for combustion control when searching for low-cost means to compensate for variabilities in natural gas composition, and for a way to determine heating value without combustion, which includes analytical determination via correlations involving $k(T_1)$, $k(T_2)$ and $\eta$, i.e., in conjunction with other properties.

Figure 1:
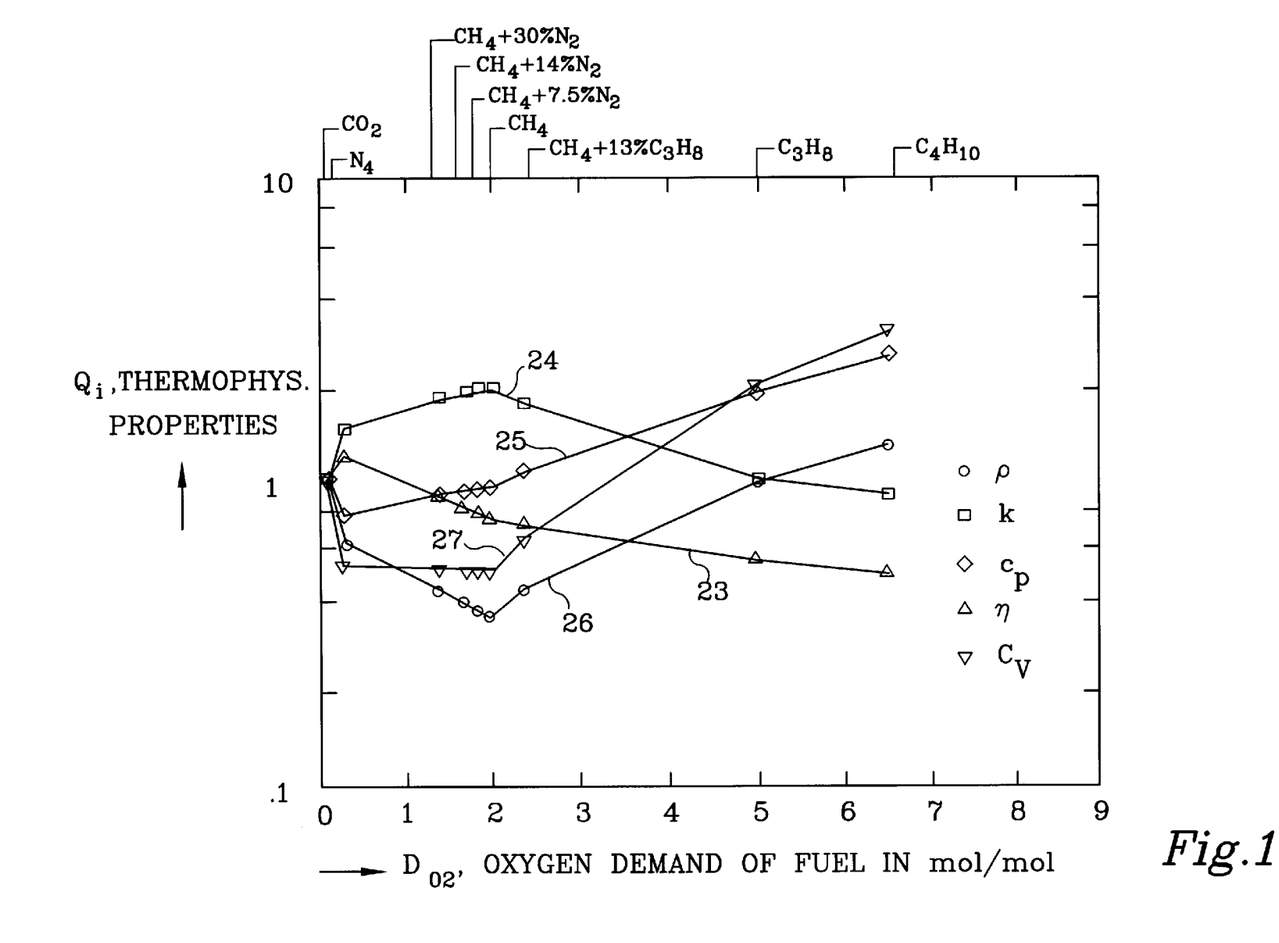
FIG. 1 is a graph of the relationship between oxygen demand of fuel and thermophysical properties of the fuel.

Here, the viscosity of the fuel, and, previously, the stack $O_2$ concentration were for indicating predicted or actual changes in the fuel's oxygen demand, $D_{O2}$. FIG. 1 shows graphically a comparison between $\eta$, curve 23, and other fuel gas thermophysical ($Q_i$) properties, i.e., $\rho$, density, curve 26; k, thermal conductivity, curve 24; $c_p$, specific heat curve 25; and $C_v$, thermal anemometer correction factor, curve 27; and how well they correlate individually with oxygen demand of fuel, $D_{O2}$. $\eta$ exhibits a most advantageous, monotonic decrease as $D_{O2}$ increases, although $c_p$ appears promising as well. The $c_p$ value of noncombustible $CO_2$ (8.83 cal/(mol·K); 8.60 for $H_2O$) lies between that of $CH_4$ and $C_2H_6$ (8.50 and 12.42), but all $\eta$-values of noncombustible gases $O_2$, $N_2$, $CO_2$ (except $H_2O$) lie above that of $CH_4$.

By including two or more fuel properties into a correlation with heating value or $D_{O2}$, the achievable accuracy increases significantly (note cited art below), but at the penalty of significant cost increases as well, because of the need for digital processing for determination of $c_p$. The above is based on the assumption that control of emissions and efficiency are prime goals of any combustion control; this is most closely achieved by operating under constant stack-$O_2$ or excess air, which in turn is met by maintaining a constant air flow and adjusting fuel flow in response to its composition variations, which change $D_{O2}$ and m*. Half of its density variation is taken care of by the factor m*, as it affects all orifice- or venturi-controlled flow control situations. The aim of adjusting fuel flow to counter variabilities in Wb, Wobb number, is similar but less correct (if one aims at conserving the A/F (air-to-fuel ratio) and emissions) and goes back to the definition of the Wobbe number, $Wb = \Delta H / m^*$, with $\Delta H$=heating value rather than $O_2$ demand and $m^* = (M_{gas}/M_{air})^{0.5}$. M is moles, Wb is closely aligned with Bn (Bonne number=$D_{O2}/m^*$), as long as non-hydrocarbon fuel constituents such as $H_2$ and CO are absent. A correlation of $D_{O2}$ or Bn with viscosity may be determined with a formula $D_{O2} = A + B\eta^C$ or $Bn = A' + B'\eta^{0.5}$, respectively. A and B are correlation coefficients and C is a correlation exponent. A' and B' are similarly correlation coefficients. The correlation is like that of natural law. Related information is in FIG. 6, page 21, of "Microsensors for Fluid Properties", by U. Bonne and D. Kubisiak, *Scientific Honeyweller*, Sensors Issue (1996). Additional information is in U.S. Pat. No. 5,486,107 by U. Bonne, issued Jan. 23, 1996 and entitled "Determination of Fuel Characteristics", which is herein incorporated by reference.

To illustrate the significance of the proposed, viscometer-based combustion control system, Table 1 compares some parameters relevant to the quality of a combustion control system based on thermal conductivity versus viscosity sensors. As shown, on all counts, the viscosity-based system lists more advantageous values such as smaller sensor output dependence on pressure and temperature but larger dependence fuel-gas composition or fuel concentration in a fuel+air mixture. The latter parameter was included to quantify the merits of direct measurement of thermo-physical properties of the fuel+air mixtures; as shown, measurement of viscosity or thermal conductivity in a premixed fuel+air mixture makes the pressure, temperature and humidity effects much larger than the sought fuel property effects. A similar case can be made for the measurement of $\eta$ or k in the stack gases.

Table 1 indicates advantages of viscosity versus thermal conductivity as $D_{O2}$ or $\lambda$, wavelength, sensors. $\lambda$=(actual fuel/air ratio)÷(stoichiometric air/fuel ratio). This table indicates that viscosity is approximately two times more sensitive to changes in $\lambda$ and $D_{O2}$ than thermal conductivity, but thirty percent less sensitive to variations in pressure and temperature. That means viscosity detection results in a several times more accurate sensor than thermal conductivity, for $D_{O2}$ or $\lambda$ measurement. The gas G20 is methane and G271 is a gas mixture of 74 percent methane and 26 percent nitrogen. p is pressure in bars, and T, temperature, is in degrees Celsius. W is the dependent variable, measuring the desired property ($\lambda$ or $D_{O2}$). Sensitivities of k and $\eta$ are relative to variability in nitrogen content of fuel mixed with air, $\lambda$, T, p and nitrogen content of pure fuel gas.

TABLE 1

| Dependence | Conditions | ∂W/∂x W = k % | W = η % |
|---|---|---|---|
| 1. ∂W(λ)/∂ (fuel + air) | G20 + air vs G271 + air λ= 1.05; 15° C. | 0.2687 | −0.3532 |
| 2. ∂W(λ)/∂λ | λ= 1.05 vs. 1.10 G20 + air | 0.0930 | −0.1229 |
| 3. ∂W($D_{o2}$)/∂Gas | G20 vs G271 (26% $N_2$) 15° C.; 1 bar | 6.7490 | −13.782 |
| 4. ∂W($D_{o2}$)/∂T | T = 20 vs T = 15° C.; G20 | 1.6320 | 1.3860 |
| 5. ∂W($D_{o2}$)/∂P | P = 2 vs 1 bar; G20; | 0.1938 | 0.1043 |

For the most desirable property (k or η), the values of W for rows 1–3 should be the highest and 4–5 the lowest. Viscosity is obviously the preferred choice.

SUMMARY OF THE INVENTION

The viscometer disclosed here does not rely on the availability of pressurized gas, a microsensor or on thermal drivers, and its output is independent of absolute pressure (to the extent that viscosity is). It is not sensitive to orientation and can be fabricated at low cost. The present viscosity sensor is used for determining the oxygen demand of various gaseous mixtures. It has a fluid volume-displacer, actuator or driver, such as a speaker membrane, and a pressure sensor or detector, such as a microphone, with a chamber or cavity and a controlled leak between the cavity and the ambient environment of the viscosity sensor. The driver, the leak and sensor electronics can be assembled from commercially available and inexpensive components. In sum, the sensor has low manufacturing costs, and good accuracy, reliability, intrinsic safety and long service life.

BRIEF DESCRIPTION OF THE DRAWINGS

FIGS. 6, 6a, 7, 7a, and 7b show additional embodiments of the viscometer.

DESCRIPTION OF THE EMBODIMENT

Figure 2:
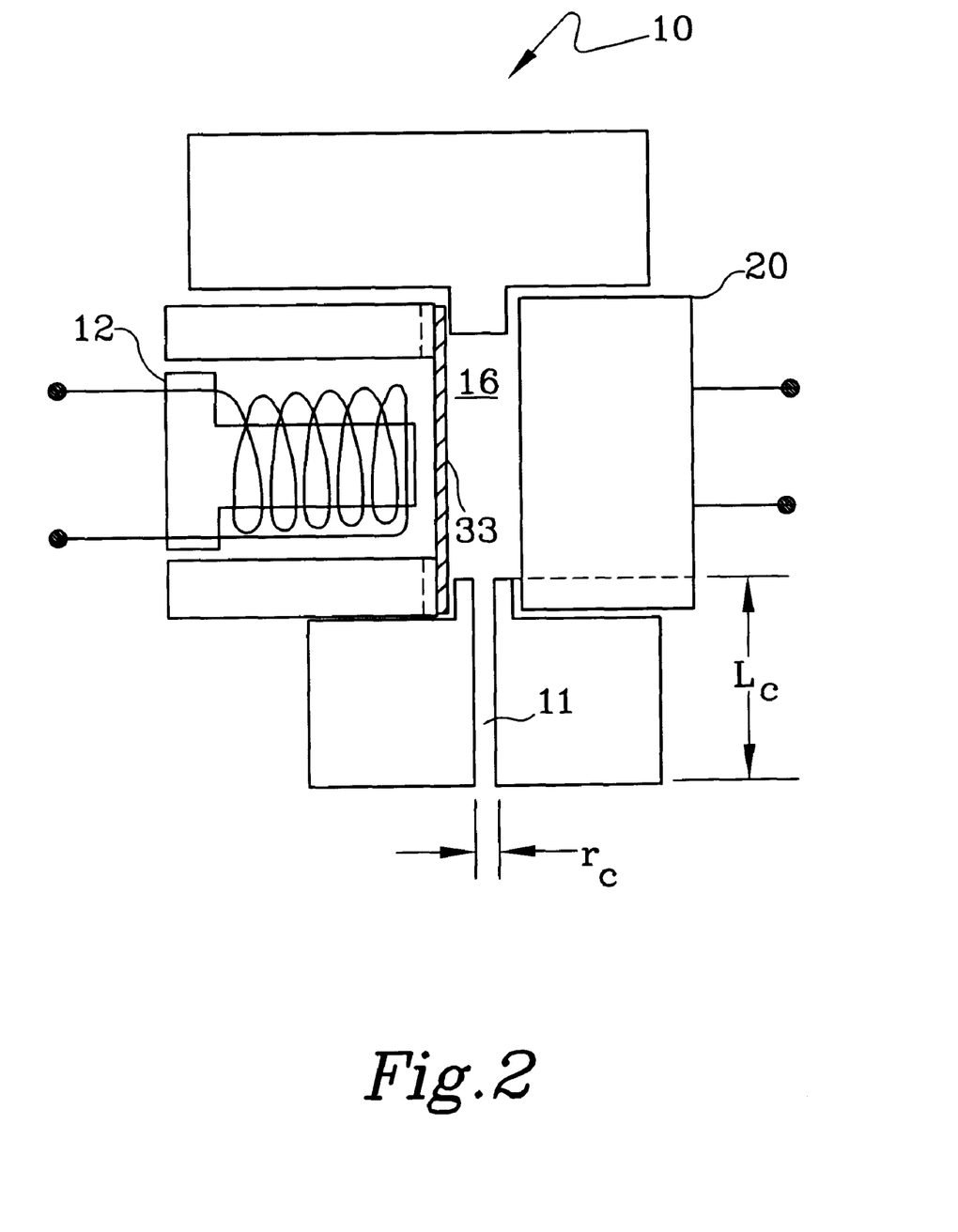
FIG. 2 shows a viscometer.

A viscometer 10 of FIG. 2 makes use of a linear relationship between laminar volumetric flow (dV/dt) through a controlled leak, for which we shall choose at first a capillary 11, (of radius, $r_c$, and length, $L_c$, of capillary tube 11) and viscosity, η, for a pressure difference, Δp. In FIG. 2, a diameter of capillary 11, 2$r_c$, is shown for clarity of the drawing. The mathematical relationship of these parameters is shown in equation (2).

$$dV/dt = \pi \Delta p r_c^4 / (8 L_c \eta) \quad (2)$$

Instead of using a thermal source, a valve or a mechanical flow is used to induce a repeatable but time-dependent flow and enable the observation of a pressure drop (or rise), Δp, time constant, τ, or phase lag, δ. Viscometer 10 disclosed here is designed to induce a repeatable but time-independent flow to enable the observation of a steady Δp when the rate of volumetric displacement by an actuator 12 and the actual leakage flow become equal for a few milliseconds (ms). This is sketched out and represented in FIGS. 3 and 4. The Δp signals for three gases, Ar, N2 and $C_3H_8$, are marked as curves 13, 14 and 15, respectively, and the volume change $\Delta V_c$, in percent, of cavity 16, shown by saw-tooth curve 17, represents the volumetric change induced by actuator or driver 12.

If it can be assumed that the displacement of a sufficiently strong actuator is independent of the type of gas, actuator 12 can be driven in a "saw tooth" mode and at constant frequency, f, and the above equation (1) indeed establishes itself; then all types of gases will eventually reach their own Δp in the chamber, but at the same capillary 11 flow rate, thus enabling the determination of each fluid's viscosity via measurement of Δp and use of equation (2). If one designs viscometer 10 to meet the first two above-noted assumptions, the remaining question is whether there will be enough time in one half-cycle to establish the above equality. If the capillary radius $r_c$ is too small, the Δp(t) will also be a saw-tooth-like function (one may neglect adiabatic heating effects for small $\Delta V_c$); but if capillary 11 is large enough, its flow and Δp will only increase until $dV/dt = \Delta V_c f / 2$, regardless of the viscosity of the gas in the viscometer 10, and then remain at that value until the end of the saw-tooth 17 period. The viscosity then results from equation (3).

$$\eta = \pi \Delta p r_c^4 / (4 \Delta V_c f L_c) \quad (3)$$

Figure 3:
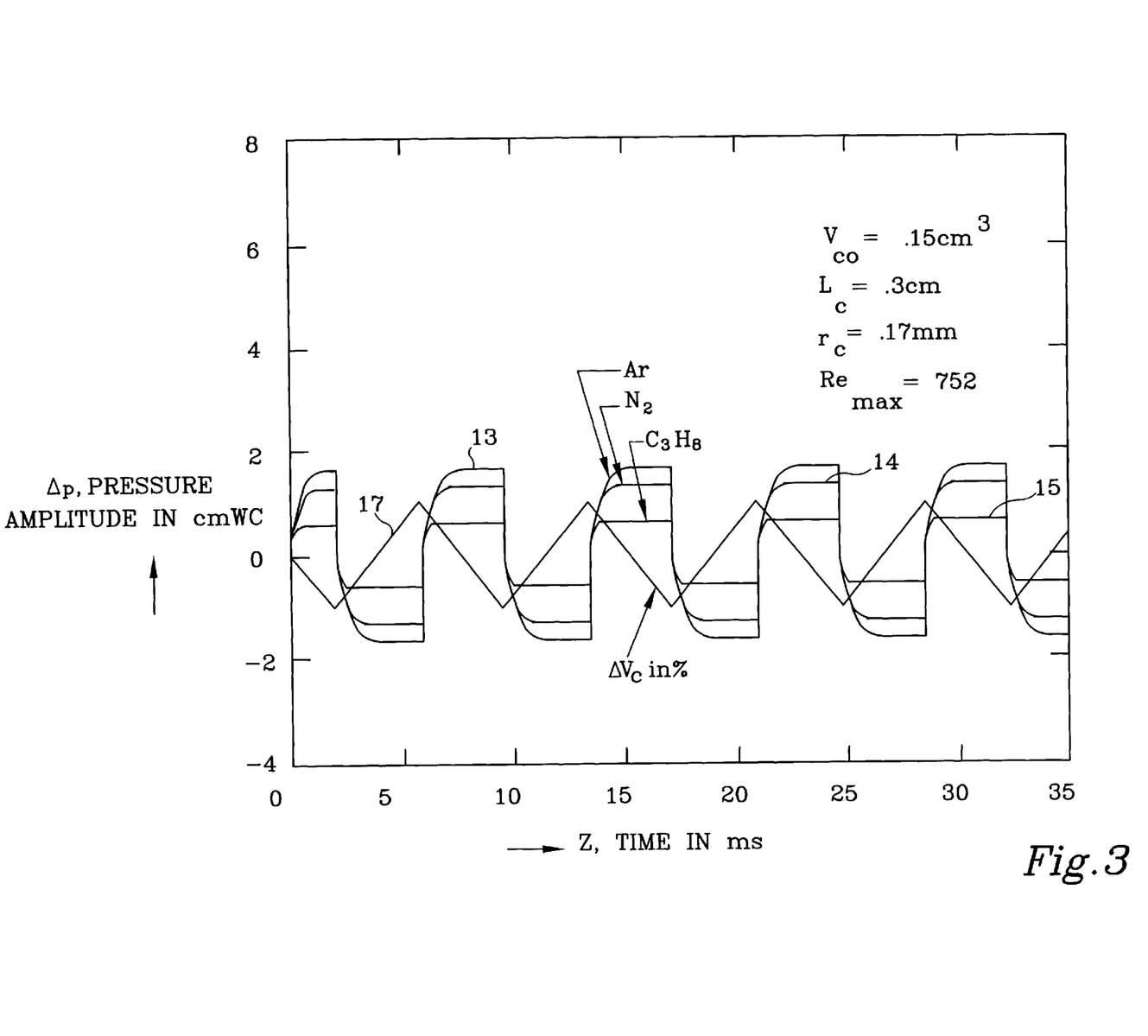
FIGS. 3, 4 and 5 are graphs of an oscillatory volume and the delta pressure of a leaky cavity for three different gases.
Figure 4:
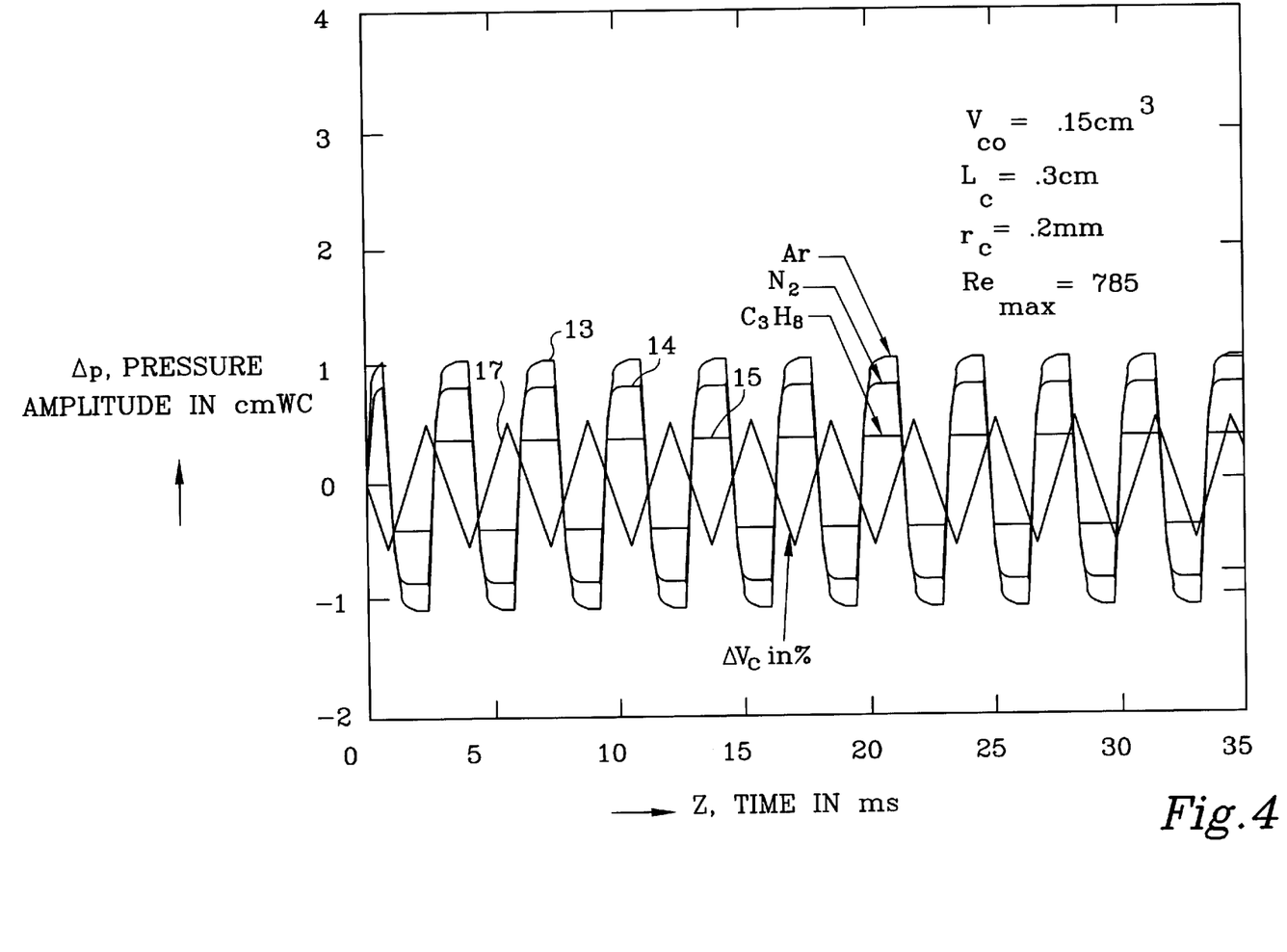

This relationship is illustrated by the results of calculations with a numerical model in FIGS. 3 and 4, whereby for a given $r_c$, $L_c$ and f, the cavity volume would be incremented by a small amount corresponding to a time step, Δz=0.1 ms, which would change the cavity pressure by an amount corresponding to PV=nRT, which in turn would start the flow through the capillary and remove some of the pressure change during Δz, until a balance between $dV/dt = dV_c/dt = \Delta V_c f / 2$ and Δp is reached. These figures show that: (1) steady Δp values can be achieved towards the end of the saw-tooth periods; (2) the values of such steady Δp periods are proportional to the viscosities of the indicated gases $C_3H_8$, $N_2$ and Ar (83, 178 and 224 μP at 20° C. and 1 atm, respectively); (3) the $R_V = \Delta V_c / V_c$, $r_c$ and $L_c$ values need to be and can be chosen to both achieve a steady Δp period and laminar flow (Re<2300) in the capillary, as indicated by the Reynolds Number, Re=2rvρ/η, for the frequencies of 124 and. 324 Hz, and the lowest η/ρ-gas, which was propane in FIGS. 3 and 4; the 324 Hz frequency was chosen to be away about equally from higher harmonics of 50 and 60 Hz; and (4) the time constants to reach the steady Δp-period are longer for higher viscosity fluids and lower pressure gases. The time constant results are illustrated in FIG. 5.

FIG. 3 is a graph of Δp, pressure amplitude in cm water column (WC) versus z or time in ms. This graph shows an oscillatory volume 17 and Δp of a leaky cavity 16 for three gases Ar, $N_2$ and $C_3H_8$, as represented by curves 13, 14 and 15, respectively. The oscillatory volume 17 of cavity 16 is the result of electrical input to actuator 12. The pressure sensor changes, as indicated by curves 13, 14 and 15, are detected by sensor 20. These plots were taken at 22° C. and a pressure of 0.7 bar. The frequency, f, is 132 Hz. $R_v$ is one percent. The pressure equilibration times to 63% of the final Δp, τ, are 0.40, 0.23 and 0.153 ms for the three gases, respectively. The cavity volume at rest, $V_{co}$, is 0.15 cm³, and capillary length $L_c$ and radius $r_c$ are at 0.3 cm and 0.17 cm, respectively. The maximum Reynolds number, $Re_{max}$, is 752.

FIG. 4 is a graph of Δp, pressure amplitude in cm WC versus time in ms, z. This graph shows an oscillatory volume 17 and Δp of leaky cavity 16 for three gases Ar, $N_2$ and $C_3H_8$, as represented by curves 13, 14 and 15. These plots were taken at 22° C. and a pressure of 0.7 bar. Frequency f is 323 Hz, which is about 2.447 times faster than f for FIG. 2. $R_v$ is 0.5%, Δz is 0.05 ms and the linear excitation, τ, is 0.18 ms. $V_{co}$ and $L_c$ are the same as for FIG. 3. The capillary radius, $r_c$, is larger at 0.2 mm. The maximum Reynolds number is 785. Note that the amplitudes of corresponding curves 13, 14 and 15 are about half of those for the curves in FIG. 3. However, the amplitude differences between curves 13, 14 and 15 appear to be more distinguishable in FIG. 4 than FIG. 3.

Figure 5:
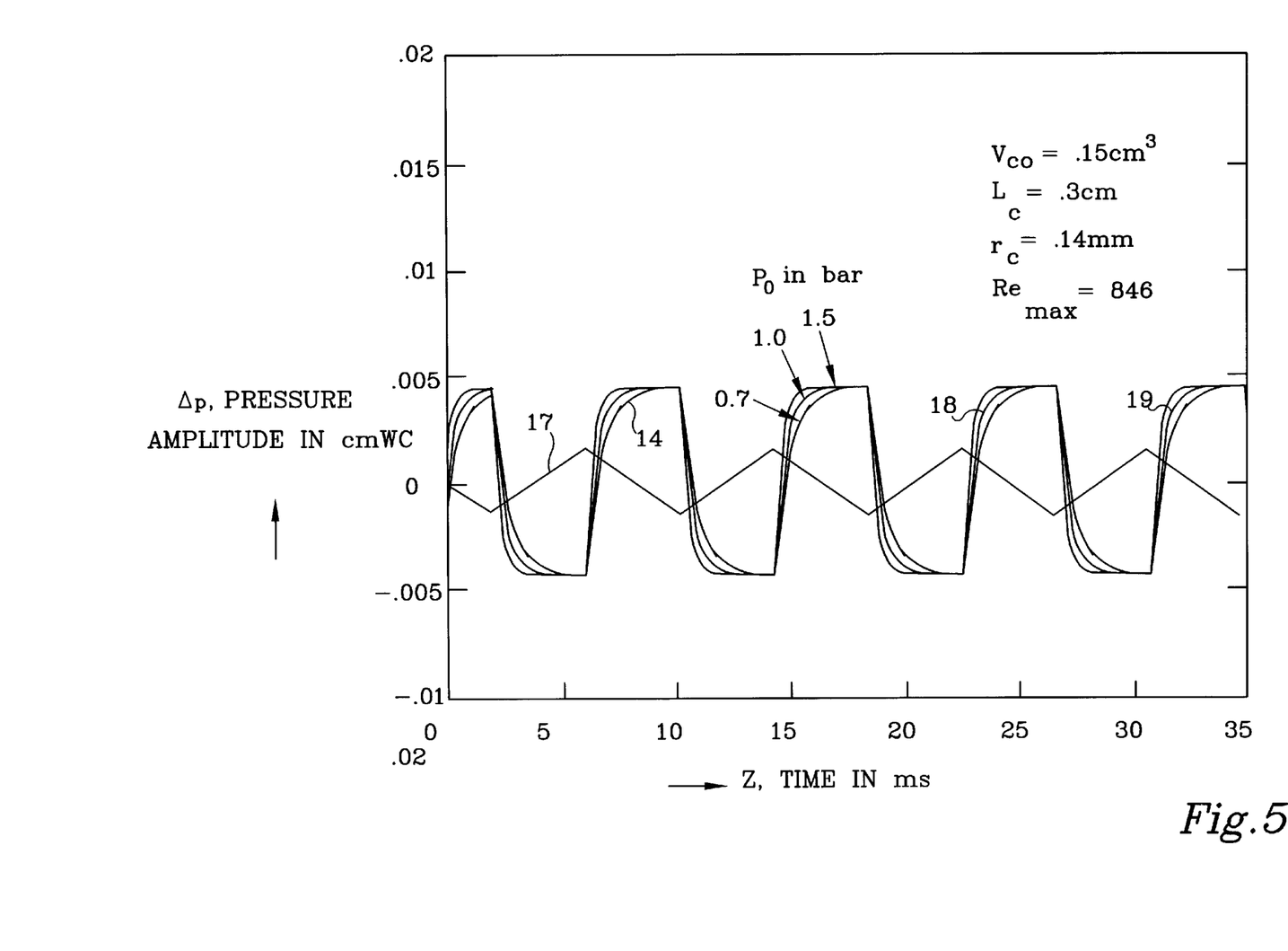

FIG. 5 is a graph of Δp, pressure amplitude in cm WC versus z, time in ms. This graph shows an oscillatory volume 17 and Δp of leaky cavity 16 for $N_2$ at three different absolute pressures, $p_a$. Curve 14 is for $N_2$ at 0.7 bar, curve 18 is for $N_2$ at 1.0 bar and curve 19 is for $N_2$ at 1.5 bar. This data was taken from device 10 at 22° C. and a frequency of 122 Hz, and $R_v$ is equal to 1%. $V_{co}$ is 0.15 cm³, $L_c$ is 0.3 cm, $r_c$ is 0.14 mm and $Re_{max}$ is at 846. These curves in FIG. 5 show that the Δp-equilibria reached are independent of absolute pressure. But they also show that the time constants to reach equilibrium, τ, are pressure dependent: time constants of about 0.29, 0.23 and 0.194 ms were derived for the pressures of 0.7, 1.0 and 1.5 bar, respectively, which may also serve to determine absolute pressure after viscosity has been determined: $p_a\tau^2 \approx$ constant.

Figure 6:
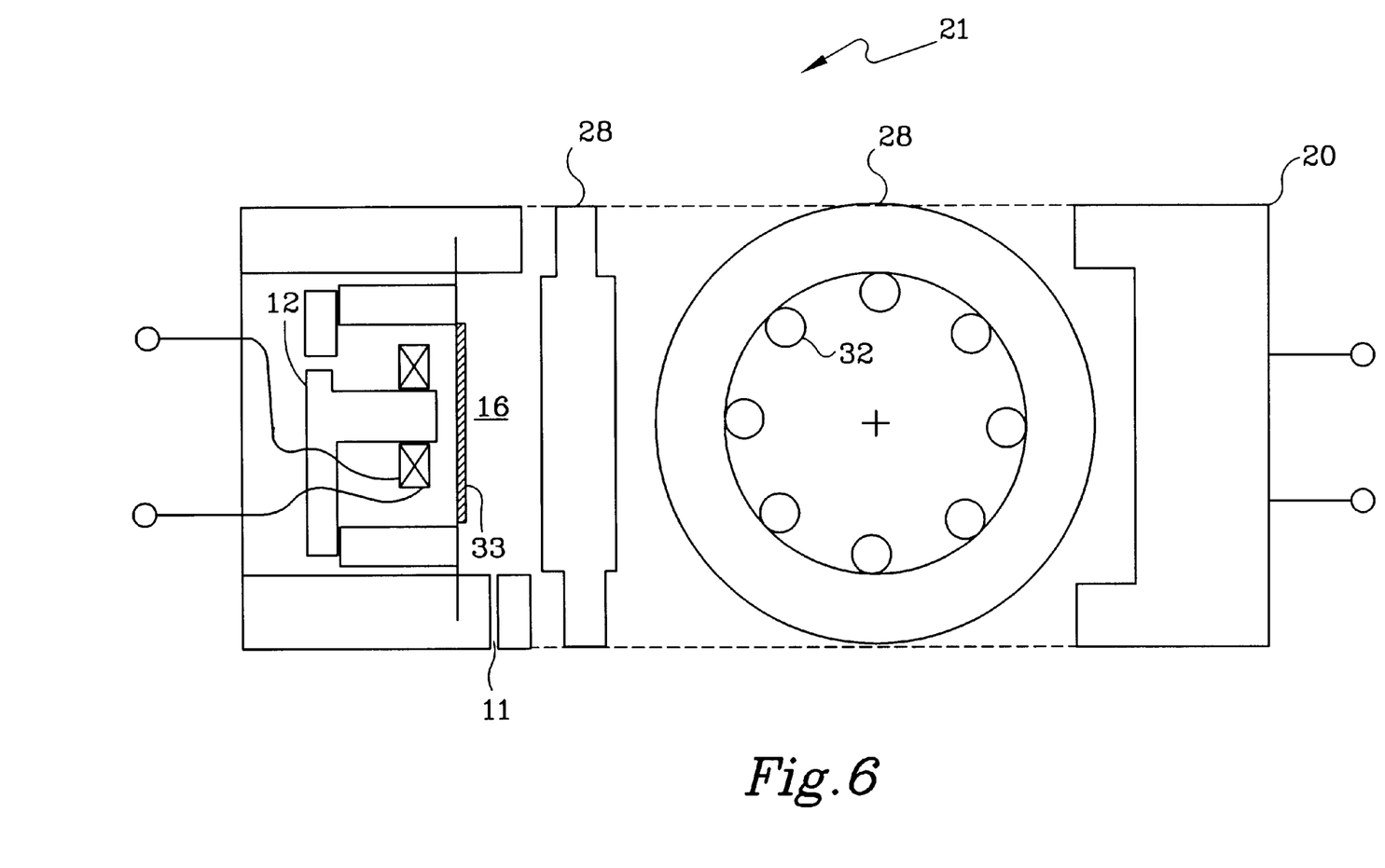
Figure 7:
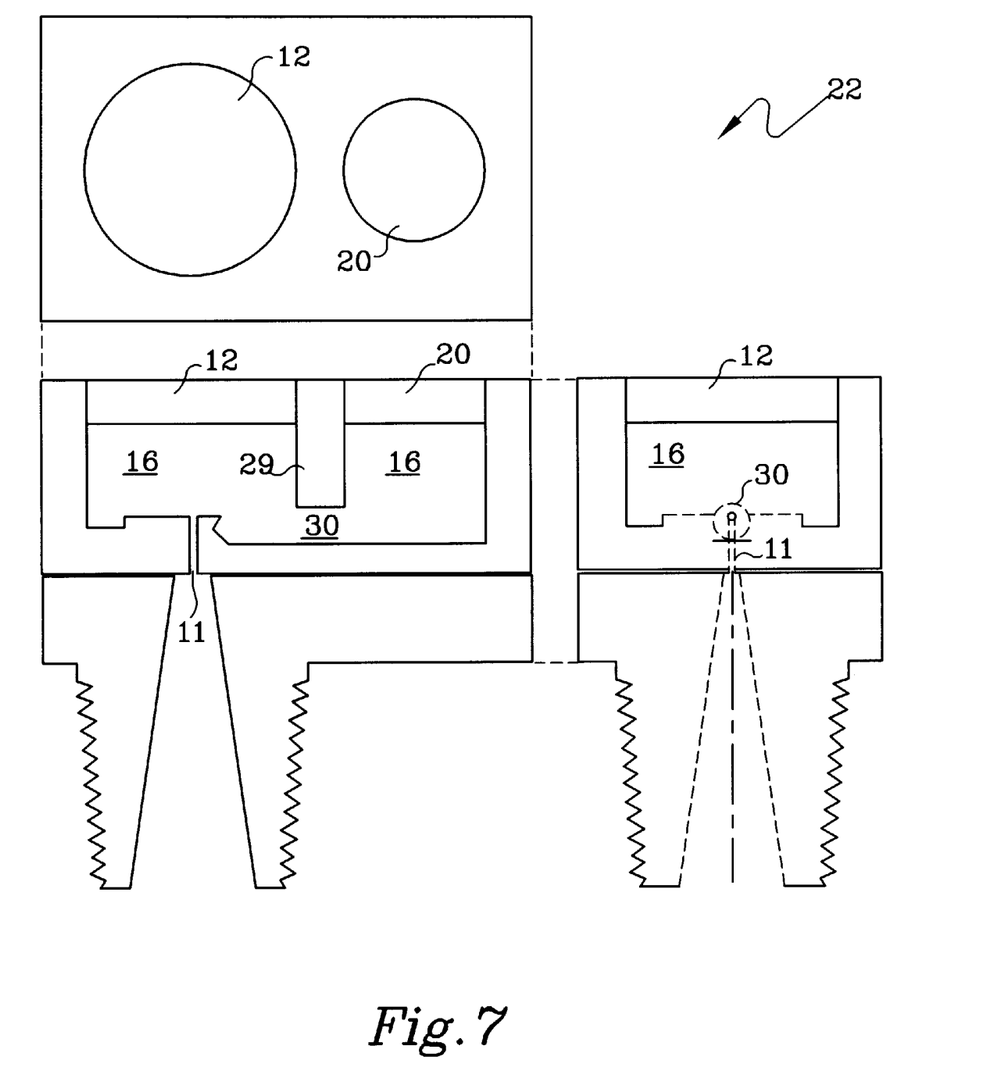

To implement viscometer 10, one needs to consider volumetric drivers 12, pressure sensors 20 and possible system limitations. FIGS. 6 and 7 show additional embodiments 21 and 22, respectively, featuring interfaces or coupling devices 28 and 29 that may be baffles or at least partial barriers between drivers 12 and sensors 20. Barrier 28 or 29 is for preventing transport from driver 12 to sensor or detector 20 any physical energy (i.e., mechanical, electrical, and/or thermal) which may hinder, delay or inhibit the transfer of Δp information from driver 12 to detector 20. Baffle 28 or 29 may prevent such possible distortion or dilapidation by effecting diffusion, attenuation or other appropriately affecting function.

Viscometer 21 has a baffle 28 situated in cavity 16 between actuator 12 and sensor 20. Baffle or diffuser plate 28 has apertures or holes 32 so that driver 12 can affect sensor 20 via the tested gas and apertures 32. The gas enters cavity 16 via capillary 11. A front view of diffuser plate 28 is shown in FIG. 6a, taken along reference line A—A in FIG. 6. Referring, now, to FIGS. 7, 7a, and 7b, viscometer 22 has a baffle, bar or damping channel 29 situated in cavity 16 between actuator 12 and sensor 20. A passage or hole 30 provides for passage of the tested gas so that driver 12 can affect sensor 20, for viscosity determination of the gas. The controlled cavity leak is though capillary opening 11.

Actuators may be of several kinds. To generate constant rate of volumetric expansion or contraction, one can consider a bulk (piezoelectric) PZT expansion, PZT bimorph actuators as used in tweeters and electromagnetic speakers as drivers 12. Volumetric expansion of piezoelectric transducers is attractive because of the large forces involved, which would not be affected by changes in gas density, although the displacements would be very small. Both PZT expansion and PZT bimorph actuators would need to be temperature-compensated, which would not be required in the instance of electromagnetic speakers.

Figure 8:
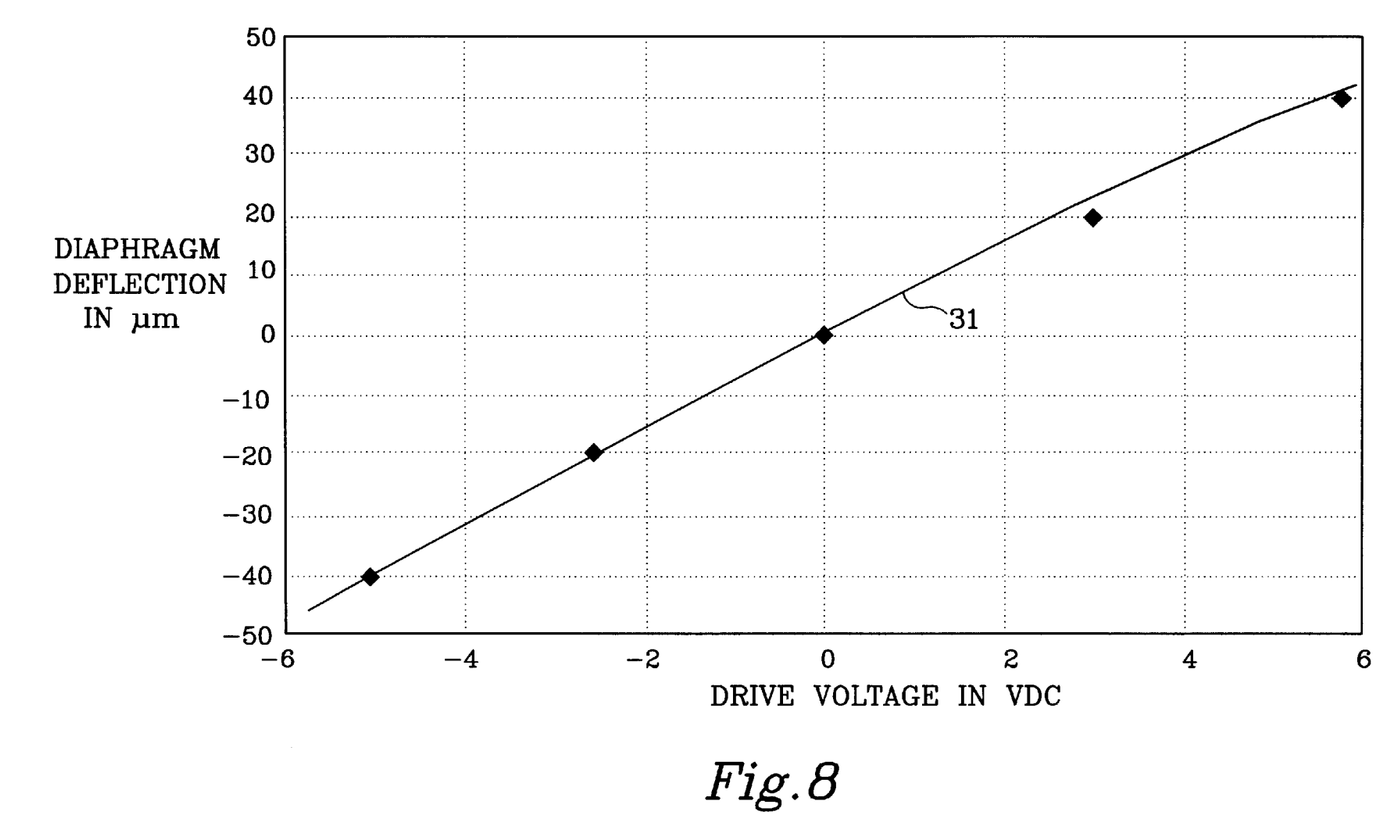
FIG. 8 is a graph of drive voltage versus deflection for an actuator of a viscometer.

Measured center deflections were made of a bimorph actuator (PZT/brass lamination by Mallory Sonalert of Indianapolis, Ind., at $0.55/each at a 25–99 quantity) consisting of a 15 mm OD/0.11 mm-thick brass support+ a 10 mm OD/0.11 mm-thick PZT+9 mm OD/0.02 mm-thick Ag electrode film. Under the rated voltage of ≦25 V, the center deflection was about 0.8 μm/VRMS. Center deflection measurements were also made of an electromagnetic speaker (BRT1209P-01, from Int'l. Components Co. of Melville, N.Y., at a price for a quantity of 25–99 at $0.60/each) and rated at a maximum input of 1–2 VDC and 10 mA maximum. The center displacement of this 50 μm-thick speaker disc was found to be fairly linear with input voltage (see curve 31 of FIG. 8). The displacement amounted to about 7.5 μm/volt from −6 to +6 VDC. This displacement per volt (V) is thus about 10 times greater than the one from a PZT bimorph. Support of the speaker membrane 33 merits some careful consideration (note membrane 33 of designs 10 and 21 of FIGS. 2 and 6, respectively).

Referring to FIG. 6, if chamber or cavity 16 is sealed to eliminate leaks across speaker membrane 33, then the side opposite to its $V_c$ side needs to be opened to an ambient/external fluid to avoid anomalous effects when the ambient pressure or temperature changes. If the volume on the membrane 33 side opposite of the cavity 16 side is not sealed leak-tight from cavity 16 (as in BRT1206P-01), then it competes with capillary 11 and/or the leak functions as an orifice.

Sensors may be of several kinds. Another function needed for viscometer 10 is the Δp sensor 20 between ambient and $V_c$. Microphones may be the lowest-cost choice to meet that need. The ideal sensor 20 would be a rigid microphone, i.e., lack of influence on $V_c$ via deformation, with a frequency-independent output. An electret microphone (by Panasonic of Secaucus, N.J., or Gentex of Carbondale, Pa., with a deformable membrane) was used in phase lag measurements. It provided an unamplified output of 200 mV for about 50–60 Hz pressure variations of ≦1.2 cm of WC. The noise level was at 2 mV, which is equivalent to (1.2/1000) (2/200)·10⁶=12 ppm of pressure change in cavity 16, or 0.012 cm of $H_2O$.

An electromagnetic speaker (BRT1209P-01 by Int'l. Components Co.), was tested as a sensor 20, back-to-back to a similar unit serving as a driver 12. However, their magnetic fields interfered, and thus shielding would be needed for good results.

A MICRO SWITCH 24PC pressure sensor chip, from Honeywell Inc. of Freeport, Ill., mounted and sealed on a TO5 header (over a center hole to avoid any back-pressure build-up) served well as a sensor 20, in operation with one of the BRT1206P-01 speakers serving as an actuator 12. It was verified that the sensor 20 output followed the shape of the driver 12 excitation (sine, square or saw-tooth shape) with capillary 11 plugged. After unplugging the capillary, a balance between rate of cavity 16 volume change and capillary 11 flow was achieved, demonstrating the invention. During this dynamic balance, the established Δp was representative of the fluid viscosity. The length to diameter ratio of the capillary 11 tube should be greater than four. The capillary 11 inlet should be smooth internally and at the edges to minimize turbulence.

Experiments with the same driver 12, but a piezoelectric speaker serving as sensor 20, yielded a pressure-independent relationship that was as expected theoretically, $\eta \approx \Delta G p^0$ (where ΔG=pressure sensor output and p=absolute pressure) within a ±5% scope measurement error. This viscosity sensor consisted of simply epoxying an available $0.60 driver 12 and $0.55 sensor 20 back-to-back, and being operated at 60 Hz. In summary, very low-cost, off-the-shelf components show that fabrication of the present viscometer 10, 21 or 22 can be very cost-effective.

Viscometer 10 may have several limitations. First, one possible limitation is head pressure due to flow reversal. As the frequency of a flow driver increases, the inertial pressure generated at each reciprocating flow reversal increases. In order to stay away from such effects, one may calculate the frequency at which the capillary 11 pressure drop, $\Delta p_c$, would equal the inertial pressure drop, $\Delta p_i$, as shown by equation (4).

$$\Delta p_c = (\Delta V_c f/2) \cdot 8\eta L_c/(\pi r_c^4) \text{ and } \Delta p_i = 2\rho v^2/2 = \pi(\Delta V_c f/(2\rho r_c^2))^2 \quad (4)$$

With the assumption that the steady volume flow in each direction, $\Delta V \cdot f/2$, generates an average velocity, $v = \Delta V_c f/(2\pi r_c^2)$, and an inertial pressure pulse upon reversal of $2\rho v^2/2$, then for $\Delta p_c = \Delta p_i$, one gets $$8\eta L_c = \rho \Delta V_c f/(2\pi) \text{ and } f = 16\pi \eta L_c/(\rho \Delta V_c). \quad (5)$$

For $\eta = 0.000178$ g/(cm·s) or $v = \eta/\rho 0.153$ cm$^2$/s for $N_2$ at 20° C. and 1 bar, $L_c = 1$ cm and $V_c = 0.0001$ cm$^3$, one gets f=77 kHz. For most applications, one will therefore be able to neglect this effect because it is generally small at low frequencies and it only occurs at each flow reversal.

Second, the appearance of turbulence in a capillary 11 tube needs to be avoided. For the above example, with r=0.008 cm, one gets $Re = 2r_c v/v = 1909$ for $N_2$ (but 6935 for propane). However, appropriately combined changes in $r_c$, $\Delta V_c$ and f, provide a laminar range that is wide indeed. To minimize the onset of turbulence, the edges at the ends of capillary 11 should be made smooth.

Third, The stability of the actuator, $\Delta p$, sensor and controlled leak (no plugging with time) are clearly critical to long-term, reliable service. The way to maintain stable displacement via circuitry, stable leak via a multiplicity of leaks in porous plate, and self-checking the sensor for proper operation and accuracy are recommended to overcome stability limitations.

The components of the quasi-static viscometer 10 and their costs, include a saw-tooth generator at $0.4, a speaker (10–15 mm diameter) at $0.22–0.25 (from DAI Ltd.), a microphone (6–10 mm diameter) at $0.22–0.25, a microphone amplifier and an analog-to-digital converter (A/D) for a digital output, at about $2.00, one or more 0.2–0.4 mm holes/capillaries of 3–6 mm in length, or equivalent controlled leaks made of porous materials, at $0.10, plus assembly, calibration and miscellaneous materials at about $3.00. Thus, the total cost of the sensor may be less than $6.00, so that its use and business potential is great.

Figure 9:
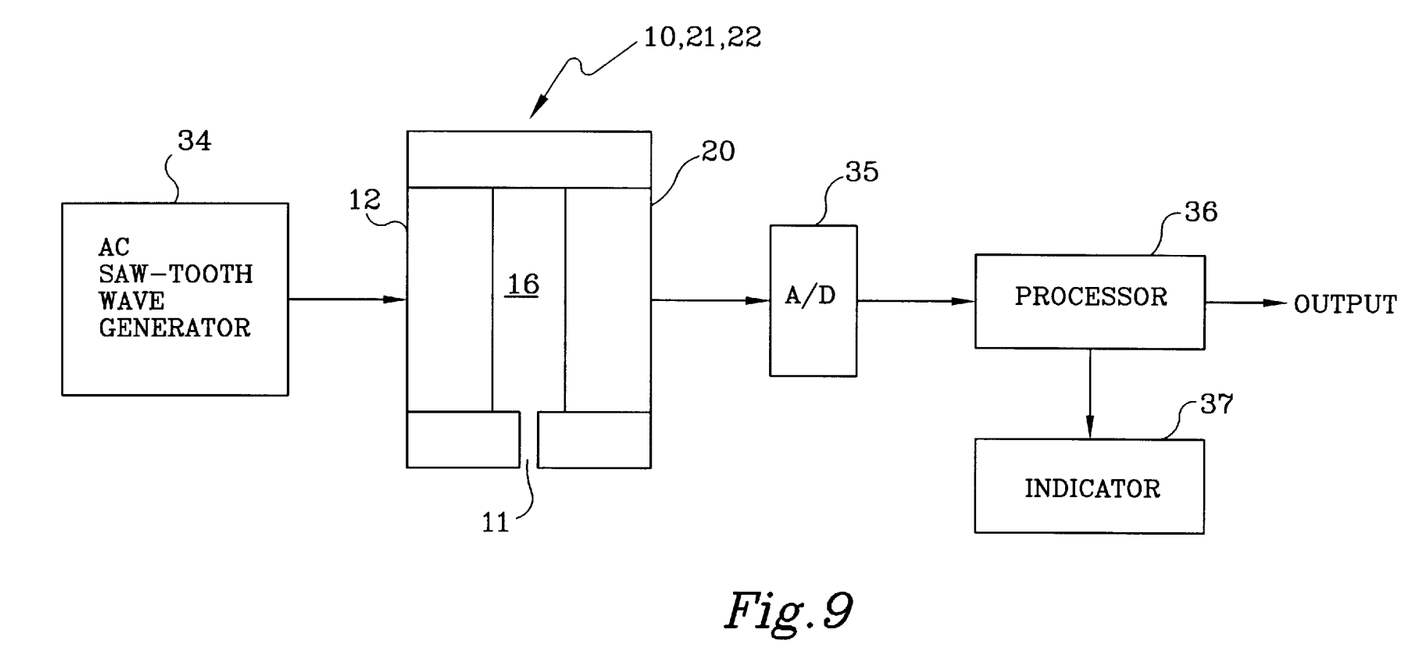
FIG. 9 shows a viscometer and associated components for use in various applications.

Referring to FIG. 9, features of the invention involve the combination of capillary 11 flow (known to be proportional to viscosity) to or from a cavity 16, an electromechanical fluid displacer/actuator 12 and a saw-tooth electronic drive 34 to enable the $\Delta p$ in cavity 16 to stabilize during at least one of the two periods of each AC actuation cycle. The measurement of the established $\Delta p$ at the end of (at least one or) each saw-tooth period is an indication of the desired viscosity. It is the $\Delta p$ (but not $\Delta p/p_a$) which is largely independent of absolute pressure, $p_a$. $\Delta p$ is sensed by sensor 20, which provides an output to an analog-to-digital converter 35, as shown in FIG. 9. The digital output goes to processor 36 for processing. Processor 36 has a digital or analog output that may be provided to some apparatus such as a combustion control or regulator. Also, an output is provided to indicator 37 that may provide readable information about the directly measured viscosity, as well as correlated properties such as oxygen demand or other parameters of the tested gas. The output of sensor 20, instead, may go directly to an anatlog indicator, processor or interface.

An embodiment may have an actuator 12 that is a low-voltage, electromagnetic earphone speaker, rather than a piezo-electric tweeter or electro-static speaker, and in which the $\Delta p$ sensor 20 is a microphone based on either piezo-electric (preferred), piezo-resistive, electro-magnetic, electret, carbon-contact or capacitance effects. The present invention may sense not only viscosity but also absolute pressure by further processing the determined viscosity and the initial time constant or phase lag between actuator 12 input and sensor 20 output, as shown in FIGS. 3–5.

Viscometers 10, 21, and 22, of FIGS. 2, 6, and 7, respectively, have advantages over related art viscometers based on vibrating wires and quartz crystal oscillators, having pressure decay<or phase lags, because they have no dependence on absolute pressure. Viscometers 10, 21 and 22 also have advantages over viscometers based on thermal excitation, because they has no dependence on thermal conductivity or specific heat of the fluid being measured. They also has advantages over traditional viscometers based on capillary flow driven by a constant source of pressurized fluid, or based on timing of the fall of an object, in that there is no need for a costly source of constant pressure fluid, constant gravity magnitude and direction, or equipment for providing and measuring the falling object. The present viscometer are not sensitive to their mounting orientations. As noted above, besides viscosity, the present devices can also be used to sense absolute pressure by using the initial time constant or phase lag between actuator input and sensor output, which is a feature not available from related art viscometers.

Other embodiments and variants of the present invention, not disclosed here, are covered by the claims and only limited in scope by the claims, which includes all equivalents thereof.

What is claimed is:

1. A quasi-static viscometer comprising:
   a driver having a diaphragm;
   a sensor having a diaphragm situated at a first distance from the diaphragm of said driver;
   a fitting formed between and around peripheries of the diaphragms of said driver and sensor to form a cavity between the diaphragms; and
   an opening formed on said fitting to provide a leak for the cavity;
   wherein said driver is capable of inducing a substantially laminar flow of a fluid within said cavity, and said sensor is capable of measuring a pressure change of the fluid in response to said driver, to cooperatively provide means for measurement of quasi-static viscosity of the fluid.

2. The viscometer of claim 1, further comprising an interface situated in the cavity between the diaphragm of said driver and the diaphragm of said sensor, wherein the cavity is divided into two subcavities.

3. The viscometer of claim 2, wherein said interface has a plurality of holes.

4. The viscometer of claim 3, wherein:
   said driver is a speaker; and
   said sensor is a microphone.

5. The viscometer of claim 4, further comprising:
   a signal generator connected to said driver; and
   a processor connected to said sensor.

6. The viscometer of claim 5, wherein said processor processes signals from said sensor into indications of viscosity of a fluid within the cavity.

7. The viscometer of claim 6, wherein said processor processes the indications of viscosity into indications of heating value, $D_{O2}$, of the fluid within the cavity.

8. The viscometer of claim 7, wherein:
said opening is a capillary tube having a length, $L_c$, and a radius, $r_c$;
said signal generator outputs a signal having a frequency, f, to said driver;
said driver causes a volume, $\Delta V_c$, of a fluid to enter and leave the cavity at a pressure variation, $\Delta p$; and
the viscosity, $\eta$, of the fluid within the cavity is equal to $(\pi \Delta p r_c^4)/(4\Delta V_c f L_c)$.

9. The viscometer of claim 8, wherein the viscosity, $\eta$, is an indication of heating value of the fluid.

10. The viscometer of claim 8, wherein the viscosity, $\eta$, is an indication of oxygen demand, $D_{O2}$, of the fluid.

11. A viscosity-based oxygen demand indicator for a fluid, comprising:
a driver having a diaphragm;
a sensor having a diaphragm proximate to the diaphragm of said driver;
a fitting having a first open end juxtaposed to said driver and a second open end juxtaposed to said sensor, and wherein said fitting, driver and sensor form a cavity; and
a leak formed in said fitting;
wherein said driver is capable of inducing a substantially laminar flow of a fluid within said cavity, and said sensor is capable of measuring a pressure change of the fluid in response to said driver, to cooperatively provide means for measurement of viscosity of the fluid, with the viscosity measurement being indicative of oxygen demand.

12. The viscosity-based oxygen demand indicator of claim 10, further comprising processor for converting signals from said sensor into indications of oxygen demand of the fluid in the leak.

13. The viscosity-based oxygen demand indicator of claim 12, wherein:
said driver is a speaker;
said sensor is a microphone; and
said leak formed in said fitting is a capillary tube.

14. A quasi-static viscometer comprising:
a structure having a cavity;
an actuator situated on said structure;
a detector situated on said structure and proximate to said actuator; and
a leak between said cavity and an environment having a fluid;
wherein said actuator is capable of inducing a substantially laminar flow of a fluid within said cavity, and said detector is capable of measuring a pressure change of the fluid in response to said actuator, to cooperatively provide means for measurement of quasi-static viscosity of the fluid.

15. The quasi-static viscometer of claim 14, further comprising an interface situated in the cavity of said structure between said actuator and said detector.

16. The quasi-static viscometer of claim 15, wherein:
said actuator has a diaphragm;
said detector has a diaphragm situated approximately in a same plane as the diaphragm of said actuator.

17. The quasi-static viscometer of claim 16, wherein said interface is situated between said actuator and detector, and is approximately perpendicular to the same plane.

18. The quasi-static viscometer of claim 17, wherein:
fluid can enter the cavity via said leak; and
fluid can pass via said interface between said actuator and detector.

19. The quasi-static viscometer of claim 18, wherein:
said leak is a capillary tube having a length, $L_c$, and a radius, $r_c$;
the diaphragm of said actuator can cause a volume, $\Delta V_c$, of the fluid to enter and leave the cavity at a pressure variation, $\Delta p$;
the diaphragm of said detector senses the pressure variation, $\Delta p$; and
the viscosity, $\eta$, of the fluid in the cavity, is $(\pi \Delta p r_c^4)/(4\Delta V_c f L_c)$.

20. The quasi-static viscometer of claim 19, further comprising a processor connected to said detector, which processes a signal indicating viscosity, $\eta$, of the fluid and determines an oxygen demand, $D_{O2}$, of the fluid.

21. The quasi-static viscometer of claim 20, wherein:
the processing to determine the oxygen demand, $D_{O2}$, of the fluid is in accordance with $D_{O2}=A+B\eta^C$; and
A, B and C are correlation coefficients.

22. The quasi-static viscometer of claim 20, wherein:
the processing to determine the Bonne number, Bn, of the fluid is in accordance with $Bn=A'+B'\eta^{C'}$;
A' and B' are correlation coefficients; and
C' is approximately 0.5.

23. The quasi-static viscometer of claim 20, wherein said processor determines absolute pressure, $p_a$.

* * * * *